(12) United States Patent
Otake

(10) Patent No.: US 8,436,117 B2
(45) Date of Patent: May 7, 2013

(54) STIMULI RESPONSIVE COMPOUND, STIMULI RESPONSIVE COMPOUND POLYMER, ACTUATOR AND METHOD FOR MANUFACTURING STIMULI RESPONSIVE COMPOUND

(75) Inventor: Toshihiro Otake, Okaya (JP)

(73) Assignee: Seiko Epson Corporation, Tokyo (JP)

( * ) Notice: Subject to any disclaimer, the term of this patent is extended or adjusted under 35 U.S.C. 154(b) by 211 days.

(21) Appl. No.: 13/019,578

(22) Filed: Feb. 2, 2011

(65) Prior Publication Data

US 2011/0196120 A1    Aug. 11, 2011

(30) Foreign Application Priority Data

Feb. 5, 2010   (JP) ................................. 2010-023811

(51) Int. Cl.
*C07D 339/06*    (2006.01)
*C08F 28/06*    (2006.01)
(52) U.S. Cl.
USPC ........... 526/256; 349/183; 526/286; 528/373; 528/377; 528/378; 549/31; 549/32; 549/35; 549/41; 549/42
(58) Field of Classification Search .................. 349/183; 526/256, 286; 528/373, 377, 378; 549/31, 549/32, 35, 41, 42
See application file for complete search history.

(56) References Cited

FOREIGN PATENT DOCUMENTS
JP    A-2005-224027    8/2005

OTHER PUBLICATIONS

Martin, G., Harms, S, Weigan, W., and Gin, D. L., "Polymerizable Transition-Metal-Containing liquid crystals with thermally reactive 1,3-diene tails", Adv. Mater. 2005, 17(5), 602-606.*
Uchiyama,Y., Ohta, A., and Fujimori, K, "Synthesis and properties of bis(1,3-benzodithiole)-type redox systems containing a xylyl rotator unit: a new type of redox-responsive molecular rotor", Heterocycles 2007, 74, 251-257.*
Ohta, A., Ueki, C., Uchiyama, Y., and Fujimoro, K., "Synthesis and properties of novel bis(1,3-benzodithiolium)-type dications containing a biaryl unit: new redox systems undergoing reversible structural changes by electron transfer", Heterocycles 2006, 69, 365-375.*
Kurata, H., Kim, S., Fujimoto, T., Matsumoto, K., Kawase, T., and Kubo, T., "Synthesis and Functionalization of 3,3'-bis-(spirodieneone)-bridged 2,2'-bithiophene: a new building block for redox-active molecular switching materials", Org. Lett. 2008, 10(17), 3837-3840.*
Feringa, B. L., "The Art of Building Small: From Molecular Switches to Molecular Motors", J. Org. Chem. 2007, 72, 6635-6652.*
van Delden, R. A., van Gelder, M. B., Huck, N. P. M., and Feringa, B. L. "Controlling the Color of Cholesteric Liquid-Crystalline Films by Photoirradiation of a Chiroptical MOlecular Switch Used as Dopant", Adv. Funct. Mater. 2003, 13(4), 319-324.*

* cited by examiner

*Primary Examiner* — Richard A Huhn
(74) *Attorney, Agent, or Firm* — Oliff & Berridge, PLC

(57) ABSTRACT

A stimuli responsive compound includes: a unit A having bonds that function as rotation axes; a first unit B disposed at a first bonding section of the unit A; a second unit B disposed at a second bonding section of the unit A; a first unit C disposed at a third bonding section of the unit A; and a second unit C disposed at a fourth bonding section of the unit A. The first unit B bonds with the second unit B by oxidation-reduction reaction, and the first unit C and the second unit C have liquid crystallinity and include polymerizable functional groups.

10 Claims, 2 Drawing Sheets

STIMULI RESPONSIVE COMPOUND, STIMULI RESPONSIVE COMPOUND POLYMER, ACTUATOR AND METHOD FOR MANUFACTURING STIMULI RESPONSIVE COMPOUND

The entire disclosure of Japanese Patent Application No. 2009-182413, filed Aug. 5, 2009 is expressly incorporated by reference herein.

BACKGROUND

1. Technical Field

The invention relates to stimuli responsive compounds, stimuli responsive compound polymers, actuators and methods for manufacturing stimuli responsive compounds.

2. Related Art

The necessity of small-sized actuators in the field of medical treatment, the field of micro-machines and the like has grown in recent years. Actuators in related art that use ion-exchange films are in the mainstream (see, for example, Japanese Laid-open Patent Application 2005-224027). Materials used therein contract and swell through ion migration, and the operation of these actuators is therefore dominated by the diffusion rate of ions, which entails many difficulties in high speed response implementation. Further, as no method exits in providing the operation of an actuator with an orientation, actuators that can realize anisotropic displacements are demanded for operating them with high efficiency.

SUMMARY

In accordance with an advantage of some aspects of the invention, stimuli responsive compounds and stimuli responsive compound polymers that are high in deformation rate and capable of deformation with an orientation, and actuators using these materials are provided. Further, a method for manufacturing stimuli responsive compounds is also provided.

In accordance with an embodiment of the invention, a stimuli responsive compound includes a unit A having bonds that function as rotation axes, a first unit B bonded to a first bonding section of the unit A, a second unit B bonded to a second bonding section of the unit A, a first unit C bonded to a third bonding section of the unit A, and a second unit C bonded to a fourth bonding section of the unit A. In an aspect, the first unit B bonds with the second unit B by oxidation reduction reaction, and the first unit C and the second unit C have liquid crystallinity and include polymerizable functional groups. As a result, a stimuli responsive compound having a high rate of deformation and capable of orientational deformation can be provided.

In the stimuli responsive compound in accordance with an aspect of the invention, it is preferred that the unit A may include bithiophene, the first unit B and the second unit B may include 1,3-benzodithiolyl groups, and the first unit C and the second unit C may include liquid crystallizable functional groups. As a result, a stimuli responsive compound having a high rate of deformation and capable of orientational deformation can be provided.

In accordance with another embodiment of the invention, a stimuli responsive compound includes bithiophene, two 1,3-benzodithiolyl groups that bond in a phases of the bithiophene, and two liquid crystallizable functional groups having liquid crystallinity that bond in β phases of the bithiophene. In an aspect, the liquid crystallizable functional groups have polymerizable functional groups. As a result, a stimuli responsive compound having a high rate of deformation and capable of orientational deformation can be provided.

In the stimuli responsive compound in accordance with an aspect of the invention, the polymerizable functional groups may preferably be vinyl groups or acrylate groups. As a result, the mobility of a stimuli responsive compound polymer that is obtained through polymerization of the stimuli responsive compound can be made higher, and the degree of deformation (deformation rate) thereof can be made higher.

In the stimuli responsive compound in accordance with an aspect of the invention, the polymerizable functional groups may preferably have a plurality of ring structures. As a result, the stimuli responsive compound has a constant orientation in its driving. In the stimuli responsive compound in accordance with an aspect of the invention, one or more halogen atoms may preferably bond with one ring structure among the plurality of ring structures. By this, the mobility of the liquid crystallizable functional groups at the time of orientation can be made higher, such that the rate of transformation to the orientation is made greater. As a result, the stimuli responsive compound can be deformed (displaced) faster and smoother, and can be driven at lower voltages.

In the stimuli responsive compound in accordance with an aspect of the invention, the polymerizable functional groups may preferably bond with the liquid crystallizable functional groups through oxygen atoms or ethylene groups. By this, the mobility of a stimuli responsive compound polymer obtained through polymerization of the stimuli responsive compound can be made higher, such that the degree of deformation (deformation rate) thereof can be made higher.

In the stimuli responsive compound in accordance with an aspect of the invention, the bithiophene and the liquid crystallizable functional groups may preferably be bonded through alkylene groups. By this, the mobility (orienting property) of the liquid crystallizable functional groups can be improved, and the orientation of deformation (driving) of the stimuli responsive compound can be made more constant.

In a stimuli responsive compound polymer in accordance with an embodiment of the invention, the stimuli responsive compound in accordance with an aspect of the invention is polymerized by the polymerizable functional groups. As a result, a stimuli responsive compound polymer having a high deformation rate and capable of orientational deformation can be provided.

In the stimuli responsive compound polymer in accordance with an aspect of the invention, the stimuli responsive compound may preferably be polymerized through double bonds or cyclohexene. By this, the mobility (orientation property) of the constituting stimuli responsive compound can be improved while retaining its orientation of deformation, and the deformation rate can be made much higher.

An actuator in accordance with an embodiment of the invention is manufactured, using the stimuli responsive compound polymer in accordance with an aspect of the invention. By this, an actuator having a high deformation rate and capable of orientational deformation can be provided.

In accordance with an embodiment of the invention, a method of manufacturing a stimuli responsive compound includes the steps of; synthesizing a compound including a unit A having bonds that function as rotation axes, a first unit B bonded to a first bonding section of the unit A, and a second unit B bonded to a second bonding section of the unit A; synthesizing a first unit C and a second unit C having liquid crystallinity and including polymerizable functional groups; and bonding the first unit C in a third bonding section of the unit A, and bonding the second unit C in a fourth bonding section of the unit A. In an aspect of the invention, the first unit B bonds with the second unit B through oxidation reduction reaction. As a result, a stimuli responsive compound having a high deformation rate and capable of orientational deformation can be provided.

DESCRIPTION OF EXEMPLARY EMBODIMENTS

Figure 1:
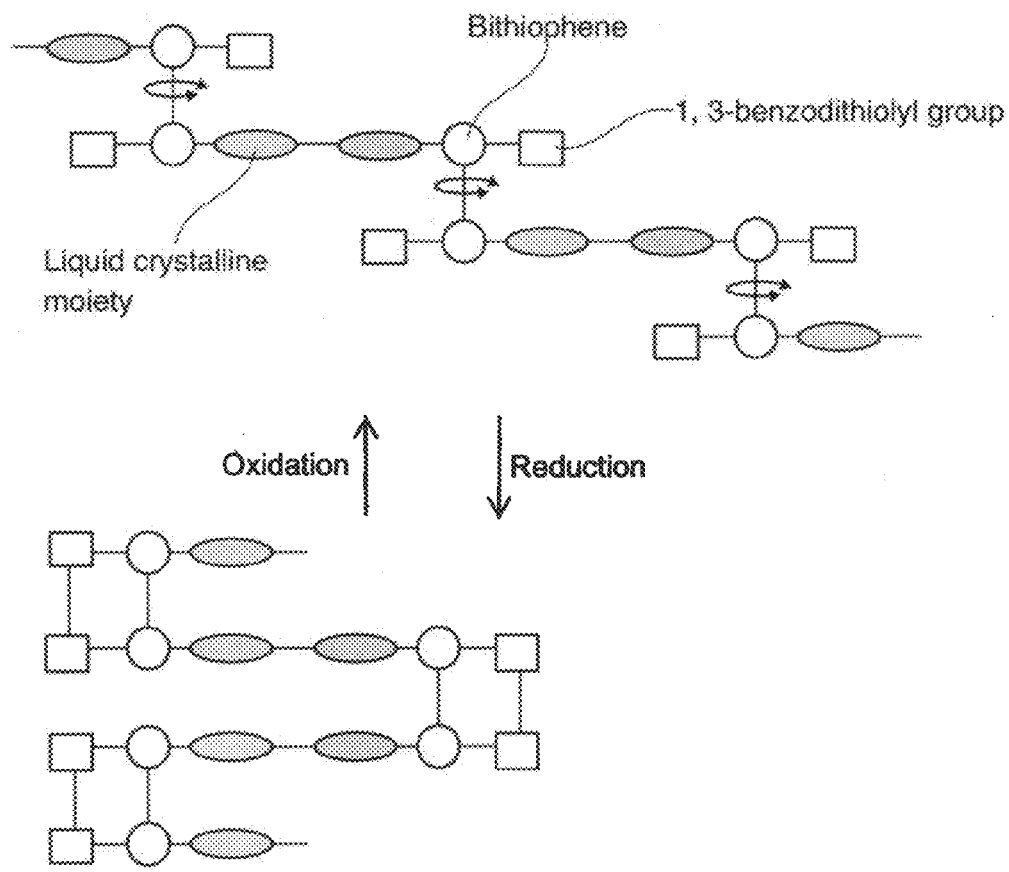
FIG. 1 is a diagram for explaining molecular structures of stimuli responsive compound polymer of an embodiment of the invention before and after oxidation reduction reaction.

Preferred embodiments of the invention are described in detail below.

Stimuli Responsive Compound

First, stimuli responsive compound in accordance with a preferred embodiment of the invention will be described in detail below. Stimuli responsive compound in accordance with an embodiment of the invention includes bithiophene (unit A), two 1,3-benzodithiolyl groups (a first unit B and a second unit B) bonded in two α phases of the bithiophene (a first bonding section and a second bonding section of the unit A), and two liquid crystallizable functional groups having liquid crystallinity (a first unit C and a second unit C) bonded in two β phases of the bithiophene (a third bonding section and a fourth bonding section of the unit A). More specifically, the stimuli responsive compound may be expressed by Formula (1) shown below, where R indicates liquid crystallizable functional groups.

[Chemical Formula 1]

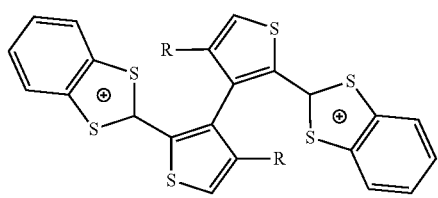

(1)

The stimuli responsive compound is a compound having a function of deforming (displacing) the configuration of molecules by certain stimulation and, more specifically, may be a compound constituting a driving section of an actuator, a micro-pump and the like. Bithiophene is a group having bonds that function as rotation axes, and capable of rotation with the bonds as axes. The stimuli responsive compound, as having bithiophene, is capable of deformation (displacement).

1,3-benzodithiolyl groups bond in two α phases of bithiophene, as shown in Formula (1) above. Also, 1,3-benzodithiolyl groups are groups that mutually form bonds among the 1,3-benzodithiolyl groups through oxidation reduction reaction. In other words, 1,3-benzodithiolyl groups are groups that form bonds upon receiving electrons from outside (being reduced). Also, they are groups that release bonds upon discharging electrons externally (being oxidized).

Because the stimuli responsive compound has 1,3-benzodithiolyl groups, the bonding state and the non-bonding state among the 1,3-benzodithiolyl groups can be reversibly and readily progressed through adjustment of its reaction condition. Also, due to its high responsiveness, the stimuli responsive compound is capable of deforming more smoothly with lower voltages. Furthermore, liquid crystallizable functional groups having liquid crystallinity (the functional groups indicated by R in the figure) bond in two β phases of bithiophene. The liquid crystallizable functional groups, as having the crystallinity, exhibit a constant orientation by the use of the liquid crystal orientation technique. By this, the stimuli responsive compound exhibits a constant orientation when driven.

The liquid crystallizable functional groups are not particularly limited to any groups as long as they exhibit liquid crystallinity, and may be groups having a plurality of ring structures, for example, a plurality of phenyl groups connected by ester groups, benzene rings or cyclohexene rings directly connected to one another, or the like. Above all, benzene rings or cyclohexene rings directly connected to one another, like those indicated by R in Formula (1) above may preferably be used, as they exhibit high liquid crystallinity.

In particular, as the liquid crystallizable functional groups, groups having a plurality of ring structures with one of the ring structures bonded with one or more halogen atoms may preferably be used. By this, the mobility of the liquid crystallizable functional groups at the time of orientation can be made higher, such that the rate of transformation to the orientation is made greater. As a result, the stimuli responsive compound can be deformed (displaced) faster and smoother, and can be driven at lower voltages.

Also, the liquid crystallizable functional groups have polymerizable functional groups. As a result, stimuli responsive compounds can be polymerized by the polymerizable functional groups. As a result, stimuli responsive compound polymer having longer molecular chains can be formed. Moreover, by making the molecular chains longer in this manner, the degree of molecular deformation (displacement) can be increased and driving with greater force (stress) becomes possible, as described in greater detail below. As the polymerizable functional groups, vinyl groups or acrylate groups may preferably be used, without any particular limitation. As a result, a stimuli responsive compound polymer that is obtained through polymerization of the stimuli responsive compound can be more readily obtained, and the mobility of a stimuli responsive compound polymer that is obtained can be made higher, and the degree of deformation (deformation rate) thereof can be made higher.

The polymerizable functional groups may preferably bond with the liquid crystallizable functional groups through oxygen atoms or ethylene groups. By such a composition, the mobility of a stimuli responsive compound polymer obtained through polymerization of a stimuli responsive compound can be made much higher, such that the degree of deformation (deformation rate) thereof can be made higher. Furthermore, the liquid crystallizable functional groups may preferably be bonded with the bithiophene through alkylene groups. By this, the mobility (orientation property) of the liquid crystallizable functional groups can be improved, and the orientation of deformation (driving) of the stimuli responsive compound can be made more constant. As specific examples of the liquid crystallizable functional groups, the following groups may be enumerated.

[Chemical Formula 2]

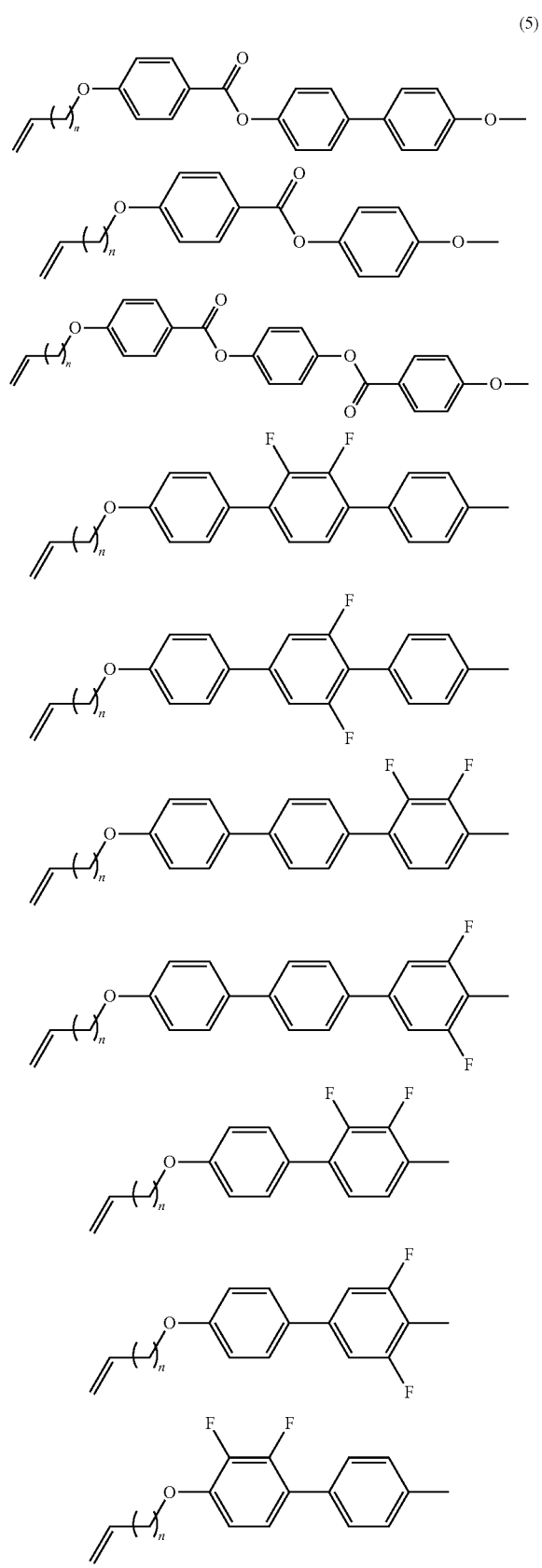

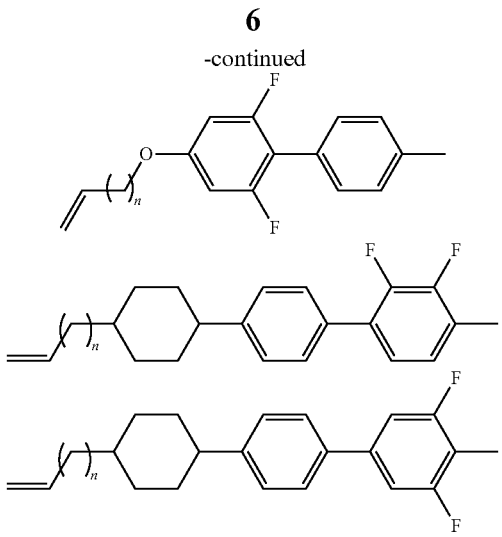

As described above, as an aspect of the invention, the stimuli responsive compound of the embodiment of the invention includes bithiophene (the unit A) capable of axial rotation, two 1,3-benzodithiolyl groups (the first unit B and the second unit B) that bond in α phases of the bithiophene (the first bonding section and the second bonding section of the unit A) and form the bonds through oxidation-reduction reaction, and two polymerizable liquid crystallizable functional groups (the first unit C and the second unit C) that bond in β phases of the bithiophene (the third bonding section and the fourth bonding section of the unit A). Due to the characteristic described above, a stimuli responsive compound having a high rate of deformation and capable of orientational deformation can be provided. Such a characteristic is thought to be derived from the following reason.

A plurality of stimuli responsive compound molecules can exist in an oriented (aligned) state due to the liquid crystallizable functional groups. Upon application of a voltage or the like to the compound molecules in the aligned state, 1,3-benzodithiolyl groups in each of the molecules are mutually bonded (cross-linked) to one another through oxidation-reduction reaction. By using the orientation property (liquid crystallinity) of the liquid crystallizable functional groups and the bonding property of 1,3-benzodithiolyl groups in this manner, a state shown in Formula (2) below on the left-hand side can be reliably deformed (displaced) to a state shown in Formula (2) below on the right-hand side. Accordingly, while deformation of the molecules can be provided with a constant orientation due to the liquid crystallizable functional groups, the degree of the deformation can be made greater by the bonding of 1,3-benzodithiolyl groups through oxidation-reduction reaction. Also, the orientation of the liquid crystallizable functional groups and the mutual bonding among 1,3-benzodithiolyl groups progress at a low voltage, such that large deformation (displacement) can be made at low voltages. Moreover, as the stimuli responsive compound has polymerizable functional groups, a stimuli responsive compound polymer having a high deformation rate and capable of orientational deformation can be readily formed.

[Chemical Formula 3]

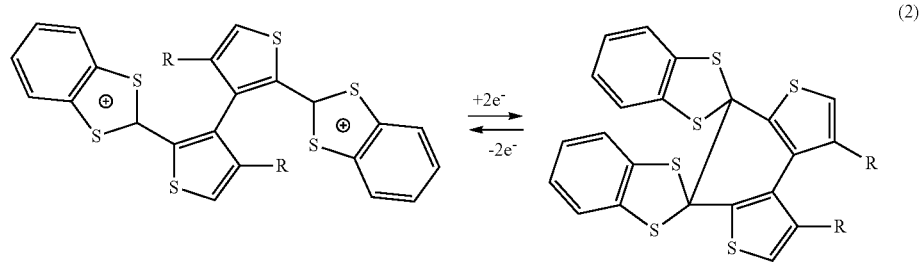

(2)

Stimuli Responsive Compound Polymer

Next, stimuli responsive compound polymers will be described. FIG. 1 is a diagram for explaining molecular structures of stimuli responsive compound polymer of an embodiment of the invention before and after oxidation reduction reaction. The stimuli responsive compound polymer can be obtained through polymerization of the stimuli responsive compound described above by polymerizable functional groups.

When polymerized, the stimuli responsive compound exists in a state in which long molecules extend in a structure shown in FIG. 1 when oxidized. By application of a voltage to give electrons to cause reduction, the molecules rotate with bithiophene as axes, adjacent ones of the 1,3-benzodithiolyl groups mutually bond to each other by oxidation reduction reaction, and further the liquid crystallizable functional groups are oriented, causing the long molecules to be in a folded state. For this reason, the degree of deformation (deformation rate) can be made greater, and the deformation can be given an orientation. In such a stimuli responsive compound polymer, the constituting stimuli responsive compounds may preferably be polymerized through double bonds or cyclohexene. By this, while the orientation of the deformation is maintained, the mobility (orientation property) of the constituting stimuli responsive compounds can be improved, and the deformation rate can be made higher.

Actuator

Figure 2:
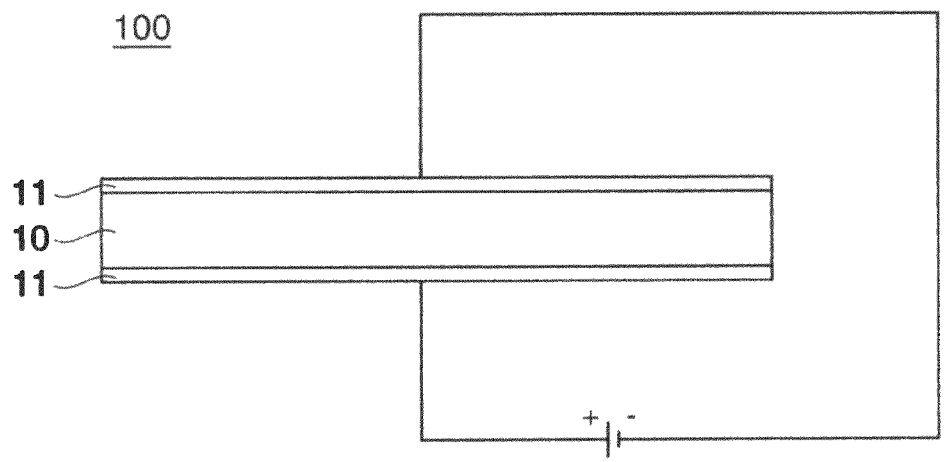
FIG. 2 is a cross-sectional view schematically showing an example of an actuator using stimuli responsive compound polymer of an embodiment of the invention.
Figure 3:
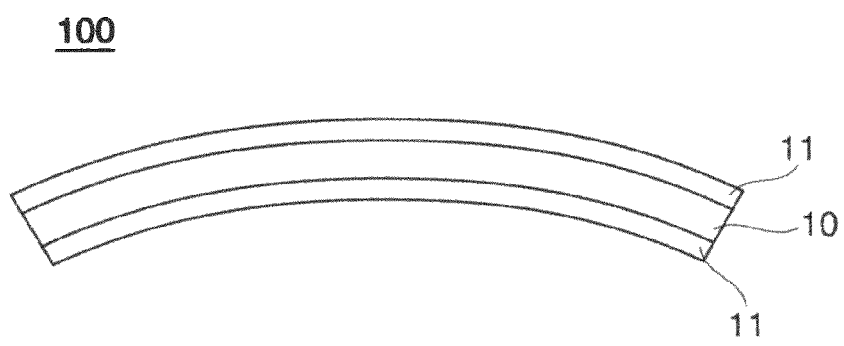
FIG. 3 is a cross-sectional view showing an example of an actuator that is deformed upon application of a voltage.

Next, an actuator that uses the stimuli responsive compound polymer (the stimuli responsive compound) described above will be described in detail. FIG. 2 is a cross-sectional view schematically showing an example of the actuator using the stimuli responsive compound polymer (the stimuli responsive compound) in accordance with an embodiment of the invention. FIG. 3 is a cross-sectional view showing an example of the actuator that is deformed by application of a voltage.

As shown in FIG. 2, an actuator 100 includes a deforming layer 10 made of a stimuli responsive compound polymer in accordance with an embodiment, and electrodes 11 provided on two surfaces of the deforming layer 10. In other words, the actuator 100 has a structure in which the deforming layer 10 is held between the electrodes 11. The deforming layer 10 is constituted of the stimuli responsive compound polymer described above, and is a layer that deforms when a voltage is applied thereto.

The electrodes 11 have a function to apply a voltage to the deforming layer 10. Also, the electrodes 11 are equipped with flexibility to follow deformation of the deforming layer 10. Orientation treatment such as rubbing treatment is applied to surfaces of the electrodes 11 that come in contact with the deforming layer 10. By this treatment, the liquid crystallizable functional groups of the stimuli responsive compound polymer can be suitably oriented. Also, by this, it is possible to exhibit anisotropy in deformation (swelling and contraction) of the deforming layer 10.

The electrodes 11 may be made of any material without any particular limitation, and may preferably be made of carbon nanotubes. By this, deformation of the deforming layer 10 can be more reliably followed. Upon application of a voltage to the electrodes 11 in the actuator 100 having the structure described above, oxidation reaction advances, causing swelling, on the side of the deforming layer 10 that is in contact with one of the electrodes 11, and reduction reaction proceeds, causing contraction, on the side of the deforming layer 10 that is in contact with the other electrode 11. As a result, the actuator 100 bends in a direction where the reduction reaction occurs, as shown in FIG. 3. Some preferred embodiments of the invention have been described above, but the invention is not limited to those embodiments.

Embodiment Examples

The invention will be described below in greater detail using embodiment examples. However, it should be noted that the invention is not limited only to those embodiment example.

Embodiment Example

An actuator shown in FIG. 2 was manufactured, using the stimuli responsive compound. The actuator was obtained by the following procedure. Stimuli responsive compound was dissolved in a solvent to form a solution, the solution was coated and dried on a Petri dish to form a dried member, the dried member (a deforming layer) was cut into a size of 3 cm×2 cm, and gold was sputtered on two surfaces of the deforming layer by using a sputter machine for making a sample for a scanning electron microscope, with an applied current of 10 mA for 30 minutes per each surface. It is noted that the stimuli responsive compound was synthesized in the following manner.

Synthesis of Iodine Compound with Bithiophene Bonded to 1,3-Benzodithiolyl Groups Dimerization and bromination using catalysts of zinc and nickel with bromo thiophene as a source material were conducted, and aldehyde groups were introduced (formylated) therein with DMF. Then, protection of the aldehyde groups was conducted, and bromine was converted to iodine. Then, deprotection was conducted, reaction with benzendithiol was conducted in the presence of an acid catalyst, treatment with 2,3-dichloro-5,6-dicyano-p-benzoquinone (DDQ) was conducted, and addition of boron tetrafluoride was conducted. As a result, iodine compound with bithiophene and 1,3-benzodithiolyl groups bonded was obtained.

Synthesis of Liquid Crystallizable Functional Groups (4-[4-(4-alkoxyphenyl)-2,3-difluorophenyl] phenylboronic acid)

First, 1,2-difluorobenzene was reacted with n-butyllithium, which was then treated with trimethyl borate, thereby obtaining (2,3-difluorophenyl)boronic acid. Then, the obtained (2,3-difluorophenyl)boronic acid was reacted with 4-alkoxy-1-bromobenzene in the presence of palladium catalyst, thereby obtaining 1-(4-alkoxyphenyl)-2,3-difluorobenzene.

Then, the obtained 1-(4-alkoxyphenyl)-2,3-difluorobenzene was reacted with n-butyllithium, which was then treated with trimethyl borate, thereby obtaining 4-(4-alkoxyphenyl)-2,3-difluorophenylboronic acid. Then, the obtained 4-(4-alkoxyphenyl)-2,3-difluorophenylboronic acid was reacted with 1,4-dibromobenzene in the presence of palladium, thereby obtaining 1-bromo-4-[4-(4-alkoxyphenyl)-2,3-difluorophenyl]benzene. Then, the obtained 1-bromo-4-[4-(4-alkoxyphenyl)-2,3-difluorophenyl]benzene was reacted with n-butyllithium, which was then treated with trimethyl borate, thereby obtaining 4-[4-(4-alkoxyphenyl)-2,3-difluorophenyl]phenylboronic acid.

Manufacture of Stimuli Responsive Compound

The iodine compound in which bithiophene and 1,3-benzodithiolyl groups are bonded underwent coupling reaction with the 4-[4-(4-alkoxyphenyl)-2,3-difluorophenyl]phenylboronic acid in the presence of palladium catalyst. Then, the compound obtained by the reaction was reacted with benzenedithiol in the presence of acid catalyst, which was then treated with 2,3-dichloro-5,6-dicyano-p-benzoquinone (DDQ), and then added with boron tetrafluoride, thereby obtaining stimuli responsive compounds.

Comparison Example 25 mg of single-wall carbon nanotubes ("HiPco" manufactured by Carbon Nanotechnologies Inc., with Fe content of 14 wt %) (hereinafter, also referred to as SWNT), 25 ml of 5 wt % of Nafion solution (a mixed solvent of low molecular weight linear alcohol and water (10%) manufactured by Aldrich), and 25 ml of reagent grade methanol were weighed and mixed in a beaker, and the mix was subjected to ultrasonic irradiation in an ultrasonic cleaner performed for more than 10 hours, whereby a mixed dispersion of SWNT and Nafion was prepared. The dispersion was casted in a glass Petri plate and left in a draft for over one whole day and night to remove the solvent. After removing the solvent, heat treatment was conducted for 4 hours at 150° C. The formed composite film of SWNT and Nafion was peeled from the Petri plate, and then cut to the size of 3 cm×2 cm. Gold was sputtered and bonded on both surfaces of the composite film, using a sputter machine for creating a sample for a scanning electron microscope, whereby an actuator was obtained. Its condition was 10 mA for 30 minutes per side.

Evaluation was conducted as follows. Test segments were cut in strips of 1 mm×15 mm from the actuators of the embodiment example and the comparison example. A 3 mm edge section of each of the sample segments was held by a holder with electrodes, a voltage of 5V is applied to the actuator in the air atmosphere, and a displacement at a position 10 mm from the fixed end was observed using a laser displacement meter. As a result, the actuator using the stimuli responsive compounds in accordance with the embodiment of the invention exhibited large displacements, but the actuator of the comparison example exhibited displacements in a smaller degree.

What is claimed is:

1. A stimuli responsive compound comprising:
a unit A having a first bond that functions as a rotation axis, the unit A including a bithiopene;
a first unit B bonded to a first bonding section of the unit A;
a second unit B bonded to a second bonding section of the unit A, the first unit B and the second unit B each including a 1,3-benzodithiolyl group;
a first unit C bonded to a third bonding section of the unit A; and
a second unit C bonded to a fourth bonding section of the unit A, the first unit C and the second unit C each including a liquid crystallizable functional group having liquid crystallinity and a polymerizable functional group; and
wherein:
the first unit B is capable of (i) forming a second bond with the second unit B when subjected to a reduction reaction and (ii) breaking the second bond with the second unit B when subjected to an oxidation reaction.

2. A stimuli responsive compound comprising:
bithiophene;
a first 1,3-benzodithiolyl group that bonds to a first α phase of the bithiophene;
a second 1,3-benzothiol group that bonds to a second α phase of the bithiophene;
a first liquid crystallizable functional group having liquid crystallinity that bonds to a first β phases of the bithiophene;
a second liquid crystallizable functional group having liquid crystallinity that bonds to a second β phases of the bithiophene,
the first liquid crystallizable functional group having a first polymerization group, and the second liquid crystallizable group having a second polymerizable functional group.

3. A stimuli responsive compound according to claim 1, wherein a first polymerizable functional group and a second polymerizable functional group are vinyl groups or acrylate groups.

4. A stimuli responsive compound according to claim 1, the polymerizable functional group having a plurality of ring structures.

5. A stimuli responsive compound according to claim 4, comprising at least one halogen atom bonding with one ring structure among the plurality of ring structures.

6. A stimuli responsive compound according to claim 1, the polymerizable functional group bonding with the liquid crystallizable functional group through an oxygen atom or an ethylene group.

7. A stimuli responsive compound according to claim 1, the bithiophene and the liquid crystallizable functional group bonding through an alkylene group.

8. A stimuli responsive compound polymer comprising the stimuli responsive compound recited in claim 1 that is polymerized by the polymerizable functional group.

9. A stimuli responsive compound polymer according to claim 8,
the stimuli responsive compound being polymerized through a double bond or cyclohexene.

10. An actuator comprising the stimuli responsive compound polymer recited in claim 8.

* * * * *